(12) United States Patent
Goldstein

(10) Patent No.: US 9,352,260 B2
(45) Date of Patent: May 31, 2016

(54) LABORATORY APPARATUS

(71) Applicant: David Goldstein, Portland, OR (US)

(72) Inventor: David Goldstein, Portland, OR (US)

( * ) Notice: Subject to any disclaimer, the term of this patent is extended or adjusted under 35 U.S.C. 154(b) by 281 days.

(21) Appl. No.: 13/903,209

(22) Filed: May 28, 2013

(65) Prior Publication Data

US 2013/0247767 A1   Sep. 26, 2013

Related U.S. Application Data

(63) Continuation of application No. 13/285,177, filed on Oct. 31, 2011, now Pat. No. 8,973,585.

(51) Int. Cl.
*A24F 5/00* (2006.01)
*B01D 46/00* (2006.01)
*B01D 46/10* (2006.01)
*B01D 53/14* (2006.01)
*B01D 47/02* (2006.01)
*B01D 50/00* (2006.01)
*B01L 5/04* (2006.01)
*A24F 1/30* (2006.01)
*A24F 9/00* (2006.01)
*G01N 1/40* (2006.01)

(52) U.S. Cl.
CPC .............. *B01D 46/0023* (2013.01); *A24F 1/30* (2013.01); *A24F 9/00* (2013.01); *B01D 46/10* (2013.01); *B01D 47/021* (2013.01); *B01D 50/004* (2013.01); *B01D 50/006* (2013.01); *B01D 53/14* (2013.01); *B01L 5/04* (2013.01); *B01D 2221/10* (2013.01); *B01L 2300/0681* (2013.01); *B01L 2400/049* (2013.01); *G01N 2001/4066* (2013.01)

(58) Field of Classification Search
USPC .......................................... 131/173
See application file for complete search history.

(56) References Cited

U.S. PATENT DOCUMENTS

| | | | |
|---|---|---|---|
| 2,487,539 A | 10/1949 | Johnstone | |
| 4,031,905 A * | 6/1977 | Dunn | 131/173 |
| 4,201,230 A * | 5/1980 | Howell, Jr. | 131/173 |
| 4,363,639 A | 12/1982 | Gladon | |
| 6,067,993 A * | 5/2000 | Mahoney, III | 131/173 |
| 2011/0094524 A1* | 4/2011 | Glover | 131/224 |

* cited by examiner

*Primary Examiner* — Duane Smith
*Assistant Examiner* — Adam W Bergfelder
(74) *Attorney, Agent, or Firm* — J. Curtis Edmondson; Law Offices of J. Curtis Edmondson

(57) ABSTRACT

The present invention relates to a glass laboratory apparatus that eliminates a pre filter and a provides a simpler vaporizing platform in fluid communication with a fitted disc filter arranged in an exhaust chamber to scrub solids from a gas using water filtration. A preferred embodiment of the present invention includes a main vessel adapted to hold a volume of a liquid such as water and an inlet conduit with an opening above the liquid level in the main vessel. The inlet conduit includes a vaporizing platform with a platform having four ventilated regions surrounding the platform.

7 Claims, 8 Drawing Sheets

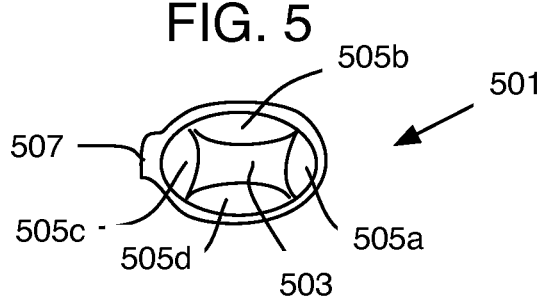
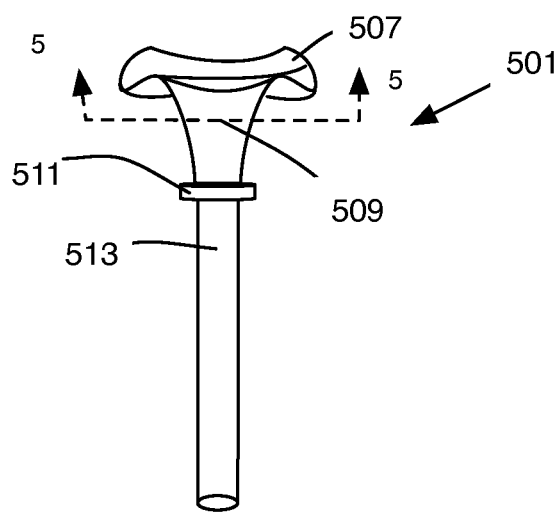
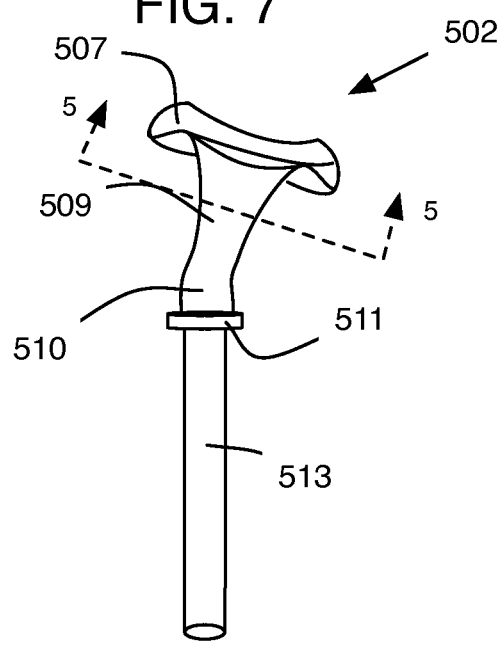

LABORATORY APPARATUS

PRIORITY

This is a Continuation-in-Part (CiP) application to the pending, non-provisional utility patent application Ser. No. 13/285,177 filed on Oct. 31, 2011. The present application is based on and claims priority from this application, the disclosure of which is hereby expressly incorporated herein by reference.

BACKGROUND

The present invention relates to laboratory glassware and more specifically to a dual-filtering apparatus using at least one fritted disc and a pre-filter to filter out solid particles, precipitate, or residue from a gaseous substance.

Laboratory glassware generally refers to a variety of devices, traditionally made of glass, suitable for scientific experiments and other work in science, particularly for use in chemistry and biology laboratories. Glass is often preferred in such environments because it is relatively inert, transparent, heat-resistant, and relatively easy to configure as needed for a particular experiment or application. Borosilicate laboratory glass-often sold under the trade name "Pyrex," is commonly utilized as its chemical inertness, transparency, and resistance to thermal stress make it the ideal material for most wet chemistry reactions.

Other types of glass are known in this art. For example, in some applications quartz glass is used: it can withstand high temperatures and offers transparency in certain parts of the electromagnetic spectrum. In other applications, especially some storage bottles, darkened brown or amber (actinic) glass is used to keep out much of the UV and IR radiation so that the effect of light on the contents is minimized. Heavy-wall glass is used for pressure reactors.

One particularly specialized use of glass in the laboratory includes glass as a filter device. Such a glass filter, termed fritted glass, is finely porous glass mass through which gas or liquid may pass. It is made by sintering together glass particles into a solid but porous body. This porous glass body can be called a frit. Applications in laboratory glassware include use in fritted glass filter items, scrubbers, or spargers. Other laboratory applications of fritted glass include packing in chromatography columns and resin beds for special chemical synthesis.

In a fritted glass filter, a disc or pane of fritted glass is used to filter out solid particles, precipitate, or residue from a fluid (or gas), which passes through the pores in the fritted glass. In the case of a gas, a pressure difference is often required to either push or draw the gas through the fritted filter. The liquid or gas passes through the fritted filter, but any solid (larger than the porosity of the frit) will be prevented from flowing through the frit.

Fritted glass is manufactured from individual bead or particles of glass fused, or sintered, into a solid, but porous glass body. Fritted discs are made by heating glass particles or fibers at a high enough temperature that they fuse together sufficiently that they become a relatively strong mass with a desired porosity. For example, a borosilicate glass frit can be made from particulate glass or from short pieces of fiber.

The porosity of a frit is related to the mesh range of the glass beads (particles) or fibers. The mesh range of glass beads or packing determines a nominal particle size: For example, a 200-400 mesh corresponds to 37-74 $\mu m$, and are sometimes called out as 40 $\mu m$. This means that a frit with a pore size of 16-40 $\mu m$ will not clog when used to support a nominal 40 $\mu m$ packing. Commonly, a frit may be classified as a medium porosity frit having 10-15-$\mu m$ porosity, a coarse porosity frit having a 40-60 $\mu m$ porosity, or an extra-coarse porosity frit having a 170-220 $\mu m$ porosity.

A single fritted filter is a common part of laboratory glassware and such items as fritted glass funnels and fritted glass crucibles are generally known and available in this art. Such single-fritted-filter device includes a laboratory scale sparger (also known as gas diffusing stones or diffusors), a scrubber, and a gas-washing bottle (or Drechsel bottle). Such devices include a fritted glass piece fused to the tip of a gas-inlet tube. This fritted glass tip is placed inside the vessel with liquid inside during use such that the fritted tip is submerged in the liquid. To maximize surface area contact of the gas to the liquid, a gas stream is slowly blown into the vessel through the fritted glass tip so that it breaks up the gas into many tiny bubbles. The purpose of sparging is to saturate the enclosed liquid with the gas, often to displace another gaseous component. The purpose of a scrubber or gas-washing bottle is to scrub the gas such that the liquid absorbs one (or more) of the gaseous components to remove it from the gas stream, effectively purifying the gas stream.

One exemplary single fritted filter laboratory glassware, described by Johnstone in U.S. Pat. No. 248,739 issued on 25 Oct. 1949, includes two chambers, one being placed within the other so that there is an annular space between the two chambers. A single fritted disc locates in the inner chamber to scrub a gas as it enters the chamber. Another example of single fritted disc filter includes the device of U.S. Pat. No. 4,363,639 to Gladon issued on 14 Dec. 1982.

Despite the benefits of a single stage (one fritted disc) filtration device, there remains a need for an apparatus having two fritted discs, or at least one fritted disk in line with a pre-filter, or preferably a serviceable, removable pre-filter which may be a fritted glass disc or other incombustible porous medium in line with the main fritted filter disc. A dual filtration device better enables scrubbing gas from a direct combustion process, which results in solid combustion byproducts, either burned to ash or incompletely so. Separating the solids from the gas prior to filtration has two primary benefits: (1) Dry recovery of combusted or heated materials, which allows for further analysis of post process materials; and (B) Dry recovery, which prevents contamination of main filter surface by particulates and resins.

SUMMARY OF THE INVENTION

The U.S. Surgeon General's report on water pipes for tobacco use in 1963 suggested that there may be beneficial reduction of harmful constituents in tobacco smoke, gas, and/or vapor by water filtration: Accordingly, one use of the present invention includes the filtration of tobacco smoke. And, laboratory analysis conclusively demonstrates the benefits of water filtration for consuming tobacco by comparing water-filtered smoke, gas, and/or vapor versus more traditional methods of ingestion. This device is well suited to that task. Prior art has no provision for introduction of freshly produced combustion or volatilized gas into a fritted filter at the modest static pressures, as typically applied when used to smoke tobacco.

The Surgeon General's suggestion indicates the need for more definitive analysis. The apparatus of the present invention is designed and intended to provide definitive laboratory analysis as to the efficacy of water filtering tobacco smoke, gas, and/or vapor as a means of toxics reduction versus more traditional methods of ingestion. This device is well suited to this important task.

Moreover, consumer demand has anecdotally proven the value of water filtration and consumers are demanding more efficient water filtering combustion devices. Some of these newer designs have evolved into considerably more intricate forms, incorporating elements of laboratory glass fabrication into their design. Some of these designs are improvements over traditional designs dating back into the 1970's. None are well suited to actual laboratory use.

This product has widespread commercial potential as well as scientific merit because it can be used to remove volatile solids from a gas by passing the gas through a water and fritted disc filtering system wherein the aperture size determined in the manufacturing of the fritted disc determines the maximum particle size remaining suspended in an effluent stream. Further, a pre-filter is used to increase the efficiency of the main filter.

DRAWING

FIG. 5 is a top view of a vapor cup according to a second preferred embodiment of the present invention.

FIG. 6 is a front view of the vapor cup of FIG. 5.

FIG. 7 is a front view of a vapor cup according to a third preferred embodiment of the present invention.

DESCRIPTION OF THE INVENTION

Figure 1:
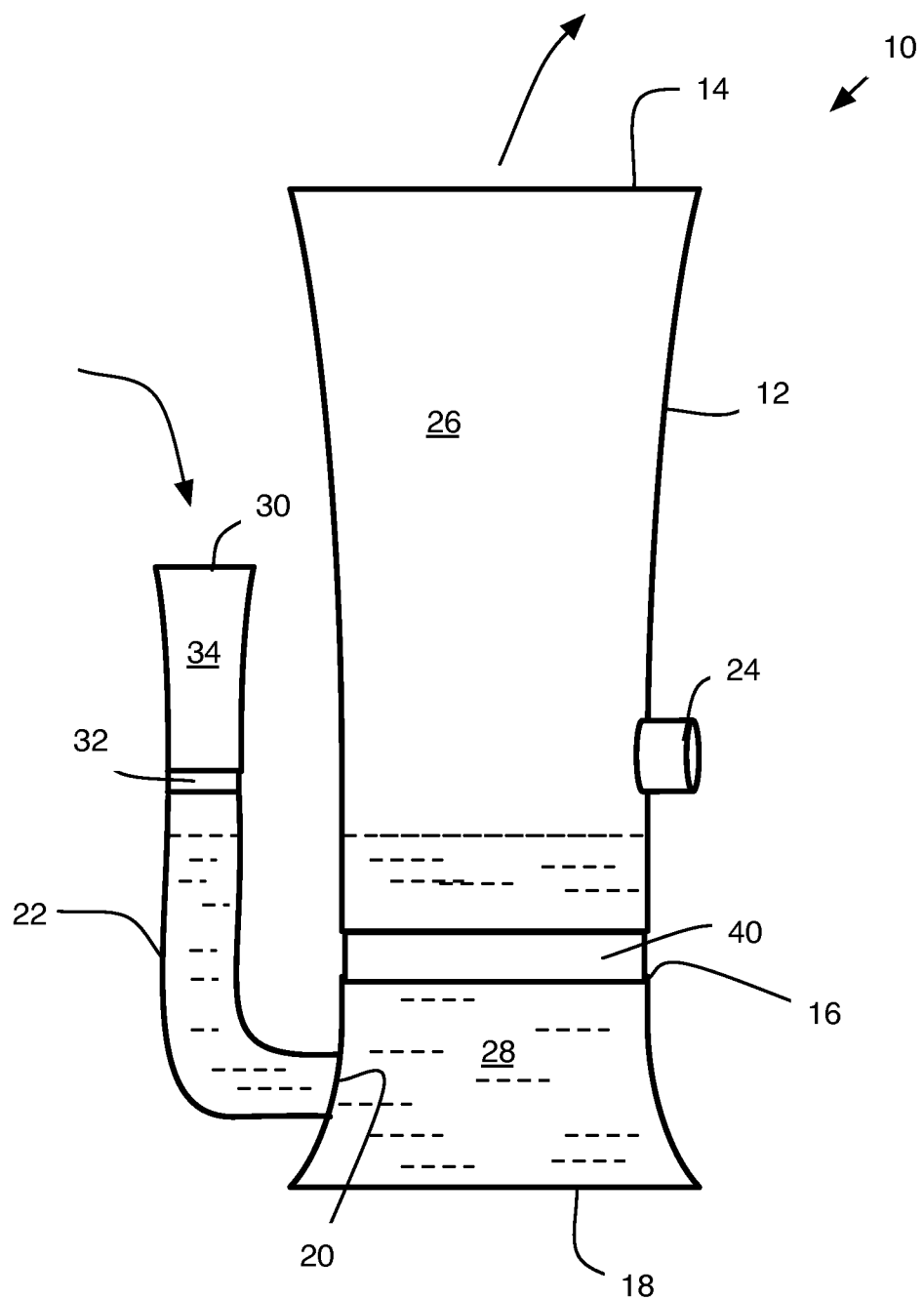
FIG. 1 is a side view of a laboratory glass apparatus according to a preferred embodiment of the present invention.

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

In one preferred embodiment, the present invention contemplates a glass laboratory apparatus filtration device having two filters. A pre-filter, which is preferably a fritted disk, although a stainless-steel mesh screen would work equally well, or a carbon fiber filter or an activated charcoal filter or other similar pre-filtering device, and a second fritted disc. The apparatus 10 includes a sample vessel 12 having an open top 14 supported by one or more sidewalls, a ledge or other similar means 16 for supporting a (second) fritted disc 40 and a bottom surface 18 having an aperture 20 connected to a downward directed conduit 22. The vessel 12 defines a chamber having a bottom and at least one sidewall with an open top and the chamber 26 is well suited for holding a liquid 28 such as water. The vessel optionally includes a relief valve 24 for selective evacuation of gas from the chamber.

In one contemplated embodiment the prefilter is a demountable, supported prefilter, which is confined to the narrow end of standard inner (male) taper ground by a close fitting outer (female) standard taper joint. Preferably, the prefilter is standardized at 15-mm to sit on $19/25$-inch inner S/T joint snugly.

In other contemplated embodiments, the first fritted disc may be substituted with any pre-filter device including a porous, incombustible pre-filter and can be configured in the vessel, for example by inverting a cone of an upturned standard-taper inner joint to form a support shelf for aforementioned pre-filter.

Figure 2:
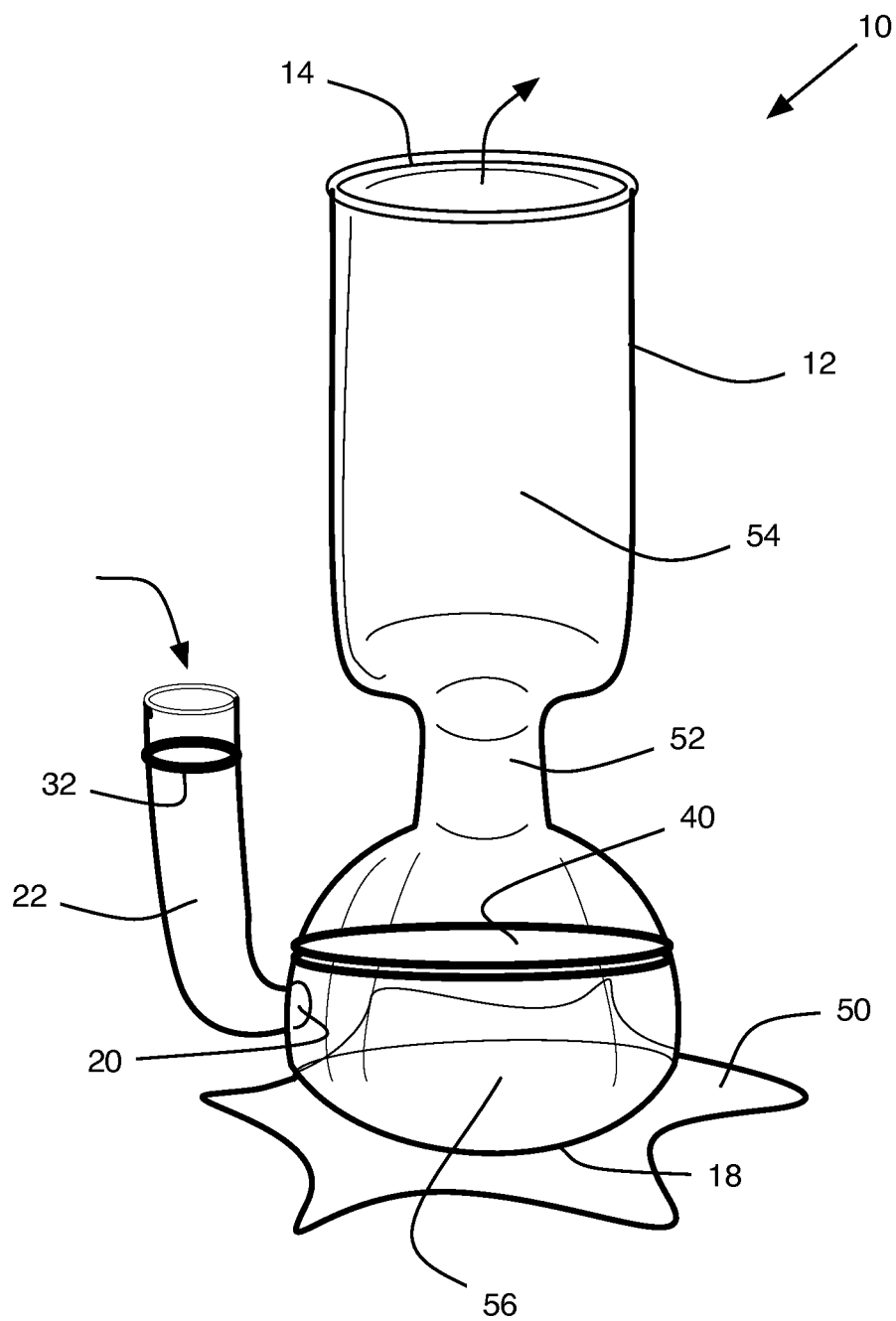
FIG. 2 is an offset frontal view of an alternative embodiment of the present invention.

As FIG. 2 illustrates, the vessel, further may include an ice shelf 52, a narrowing of the vessel's vertical sidewall to retain an ice cube or block of ice to further cool the effluent gas after the gas has exited the main filter fritted disc and has already passed out of the liquid. The ice block further cools the gaseous sample and further condenses out volatile solids that my have escaped the fluid and fritted disc. Further, the restriction of the ice shelf 52 divides the vessel into an upper chamber 54 and a lower chamber or bowl 56. The second fritted disc 40 arranges in the second, lower chamber 56 and the level of the fluid covers the filter 40 but is at a level that is below the ice shelf 52 and below the pre-filter 32.

The downward directed conduit 22, in turn, links the sample vessel 12. Specifically, the downward directed tube terminates in an opening in a sidewall 20 of the apparatus body, and this aperture is near the bottom, adjacent to a bottom wall of the main body of the apparatus. The conduit 22 has an inlet opening 30 near the top. A first fritted disc 32 fits near the open top. An inlet chamber 34 hermetically seals to the first fritted disc or other pre-filter including a stainless steel mesh or carbon fiber or other similar filter device, which is positioned such that the solution or liquid 28 rests at a level that is below the first fritted disc or pre-filter 32.

A fluid, or more precisely, a gas conduit is formed by the linking or coupling from the inlet opening 30 to the exhaust opening 14. Thus, when a pressure differentiation is affected (lower pressure at the exhaust) a gas is forced through the first fritted disc or pre filter 32 through the liquid solution 28 and up through the second disc 40.

The inlet chamber 34 includes means for burning a sample. As such, the apparatus of the present invention is well suited for scrubbing a gas of undesired particles, solids, and other impurities. Another benefit, if used with water in the main chamber, is the cooling effect of the water and that the water can trap some heavier particles and water-soluble molecules, preventing them from entering the effluent stream.

In the preferred embodiments, the first or pre-filter should be kept dry, and therefore it must be above the water level in the vessel. This is important because it becomes immediately clogged if wet. Alternatively, a check valve may be included to keep the pre-filter dry regardless of the water level in the vessel. The orifice of the vaporizing platform portion (bowl) must be sufficiently wide to allow for adequate airflow: One suitable interior diameter of such an orifice is about 6-mm. The bowl may be heated by hot air or open flame. In the case of combustion, the burning material will usually suck down through the combustion venturi orifice before it has entirely burned.

Now, regarding the combustion or vaporization of the sample, a funnel terminating in a restricted orifice of approximately 6-mm is provided so that volume of airflow is not compromised by excessive static pressure while the sample is contained in a configuration promoting efficient combustion. This combustion vaporizing platform is affixed to the body of the apparatus in an airtight fashion by means of a standard taper ground joint, in this case either 19/22-mm or 19/26-mm standard taper joint. This configuration also serves to position the pre-filter precisely on the inner joint, which supports it. The combustion/vapor generator may be made from borosilicate or quartz materials. Quartz allows for more heating options and increased durability.

The apparatus of the present invention is well suited for scrubbing a gas of undesired particles, solids, and other impurities. Another benefit, if used with water in the main chamber, is the cooling effect of the water and that the water can trap some heavier particles and water-soluble molecules, preventing them from entering the effluent stream.

One use of the present invention includes filtering gas or vapor, such as tobacco. A sample of burning tobacco is placed in the inlet chamber 34 and ordinary water is placed in the vessel as the liquid 28—this is known as water filtration and there is substantial epidemiological evidence of lower incidences of carcinoma among tobacco smokers using water filtration compared to other methods of inhaling tobacco products—i.e. from a cigarette, pipe, or cigar. The gas-dispersion frit serves to break up the smoke, gas, and/or vapor into very fine bubbles, thereby increasing its water-contact area. Frits are commonly referred to as "diffusers" for the way that they diffuse (or disperse) the particulates suspended in the gas as it exits the vessel.

The present invention can be altered physically to affect the needed pressure differential to cause bubble filtration through the two filters. The greater the volume of water, the greater the pressure differentiation required scrubbing the gas. The defined range of pressure differential is limited by water column height, which should not exceed the height of the pre-filter, as it works poorly when wet. Additionally, allowing the combusted remains to get wet would create recovery and purity issues for the research chemist.

In one suitable preferred embodiment, a laboratory apparatus 10 consists of blown glass, specifically the apparatus is fabricated from borosilicate glass tubing, 33-expansion type and includes two filters, preferably a first (pre-filter) fritted disc and second fritted disc, however the pre-filter could also be a stainless steel mesh screen or any incombustible yet porous substance, as would be appreciated by those skilled in this art. Each disc is fabricated by filling rings of high-temperature fused silica (quartz) glass with commercially available clear borosilicate frit, large size (#25 mesh) as supplied, for example by North Star Glass and/or Glass Alchemy (both located in Portland, Oreg., USA).

Alternatively, a fritted disc consists of a mullite shelf that has been core-drilled to mold size, or the fritted discs may be fused in a ceramic mold that has been perforated (by core drill) with a grid of properly sized holes to mass produce many fritted discs in a single firing, then coated with alumina-kaolin mold release, which is dried before being loaded with loose frit. This process is a faster and more economical process that is better suited to larger production quantities. Further, the plugs cut from the mullite plate will make good weights to ensure both sides of the disc are flat, for example. In other embodiments, known methods and materials for refractory type glass would also work and are contemplated in the scope of the invention.

Then, the quartz rings are placed on a mullite kiln shelf lined with ceramic kiln fusing paper on the bottom or a mold release is used, filled them with frit, and kiln fired them up to about 1550-degrees F. for about 40 minutes. Once cool, the result is a highly porous fritted disc with little resistance to flow of gas or liquid.

To avoid significant breakage of the fritted discs, a kiln wash/glass release using kaolin clay and alumina hydrate is painted the slurry on the quartz rings, dried it out, and then filled the rings with frit. Moreover, a glass release compound of kaolin clay and alumina hydrate slurry is applied to all mold surfaces to prevent damage to both molds and fritted ware upon release, as would be well understood by those skilled in this art.

The discs 32 and 40 can be made in small batches or, alternatively, for larger production quantities, fabricating the fritted discs—instead of quartz rings that need to be filled individually—from flat plate stock that has been core-drilled to the proper diameter so that many mold orifices can be filled quickly from bulk, and the leftover slug from core drilling can be used as a weight to make both sides of the disc even and parallel. Further economies can be gained from using a kiln wash as an effective substitute for more expensive and time consuming kiln paper covering the mullite kiln shelf.

In other embodiments, mullite—instead of quartz—can be used for a mold material. It is a bit cheaper (both are expensive), but easier and faster to drill holes in. Graphite would also work, but graphite oxidizes at fusing temperature, which would distort mold dimensions and be consumed without a nitrogen or inert gas atmosphere.

FIG. 2 shows a base 50 connected or fused to the vessel at a lower portion. The base aids in supporting the vessel on a level surface and, accordingly can be any shape. One contemplated shape is a hexagonal base, another contemplated shape is a six-pointed concave hexagon with curved line segments joining each adjacent point of the six points, each point equally distant from the bases geometric center; although those skilled in the art would appreciate that additional configurations for the base would work equally well. Not shown in the drawings, but contemplated nevertheless: A supporting member adapts to connect the inlet portion to the main body of the vessel, this supporting member is not in fluid connection with the inlet and outlet, but serves merely to mechanically strengthen and reduce the propensity for damage and breakage of the inlet tube portion relative to the main vessel body.

Also, in an alternative contemplated embodiment, the vessel ideally has one common outer diameter. Thus, ice shelf or restriction of the inner diameter of the vessel can be shaped during the formation of the vessel, for example it can be formed from a massive thickening of the original tube, then blown against a flat carbon paddle. This way, the OD is unchanged but the ID is restricted.

Other contemplated modifications to the present invention include accessories for glass water pipes in general. Those skilled in the art could readily adapt such known accessories to work with the present invention as shown and described herein.

The use of standard taper ground joints will allow for a variety of commercially available accessories to be used in conjunction with this product. Botanical essences can be vaporized most efficiently by means of the sheathed quartz cup as pictured in the accompanying figures of the drawing.

Other enhancements to the present invention contemplate using three or more filters in various arrangements. Further, the vessel may be made of quartz for improved durability.

Other modifications contemplated with any of the preferred embodiments include a dome structure that acts as a chimney and prevents or restricts the rate of vapor escaping—an example of this is captured in FIG. 2 wherein a narrowed opening above the water chamber acts as the chimney.

Figure 3:
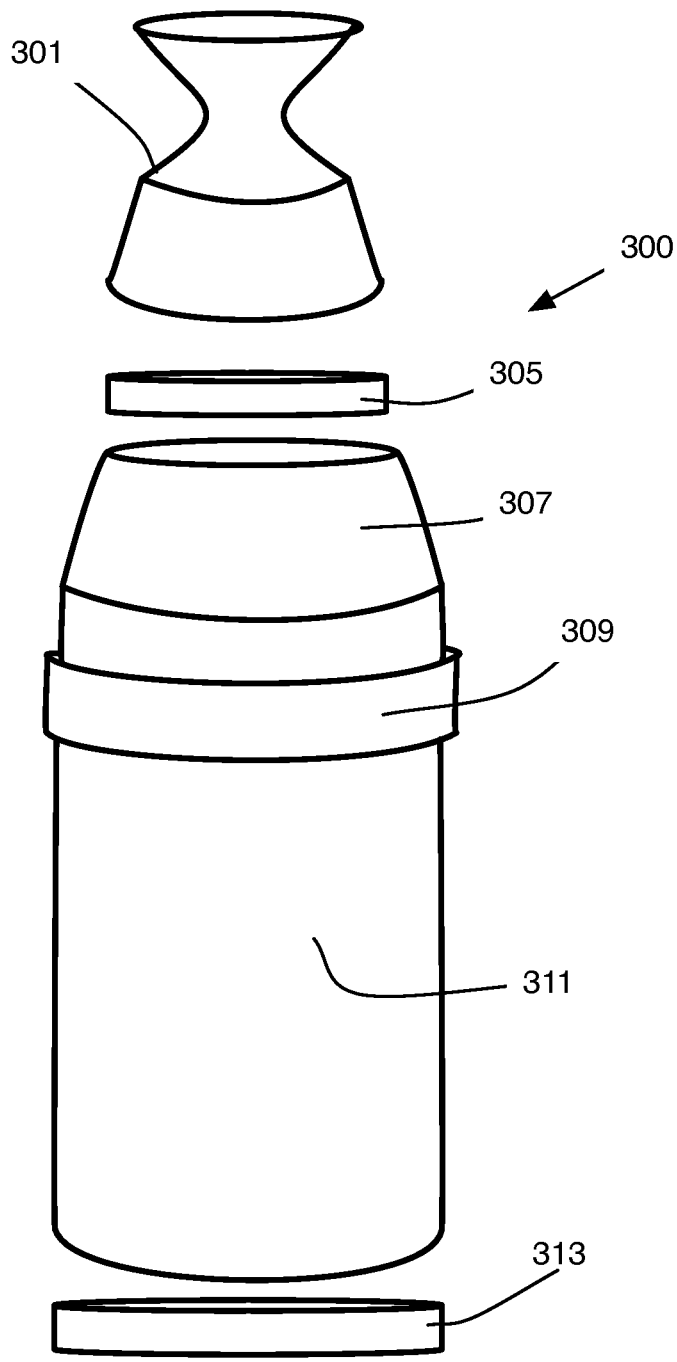
FIG. 3 is an exploded front view of a filter insert adapted to retrofit standard glassware of the prior art.

FIG. 3 shows an insert 300 adapted to fit inside the inlet chamber of glassware already known in the art and, accordingly, retrofits prior-art glassware to have a pre-filter fritted disc and a main filter fritted disc. This insert 300 fits over a standard taper and inserts under a standard chamber piece 301. The insert 300 includes a pre filter element 305, which is held in place in the tapered portion by a snug fitting rod assembly having a tapered nose 307 and cylindrical shaft portion 311. A rubber washer, o-ring or other similar stopper-type sleeve 309 fits on the shaft to snug the shaft into the vapor cup. A second pre-filter fritted disc 313 arranges at the opposite end of the shaft and fits in the inlet chamber 34 as described above, and, ideally, is fused to the bottom of the lower shaft 311.

Figure 4:
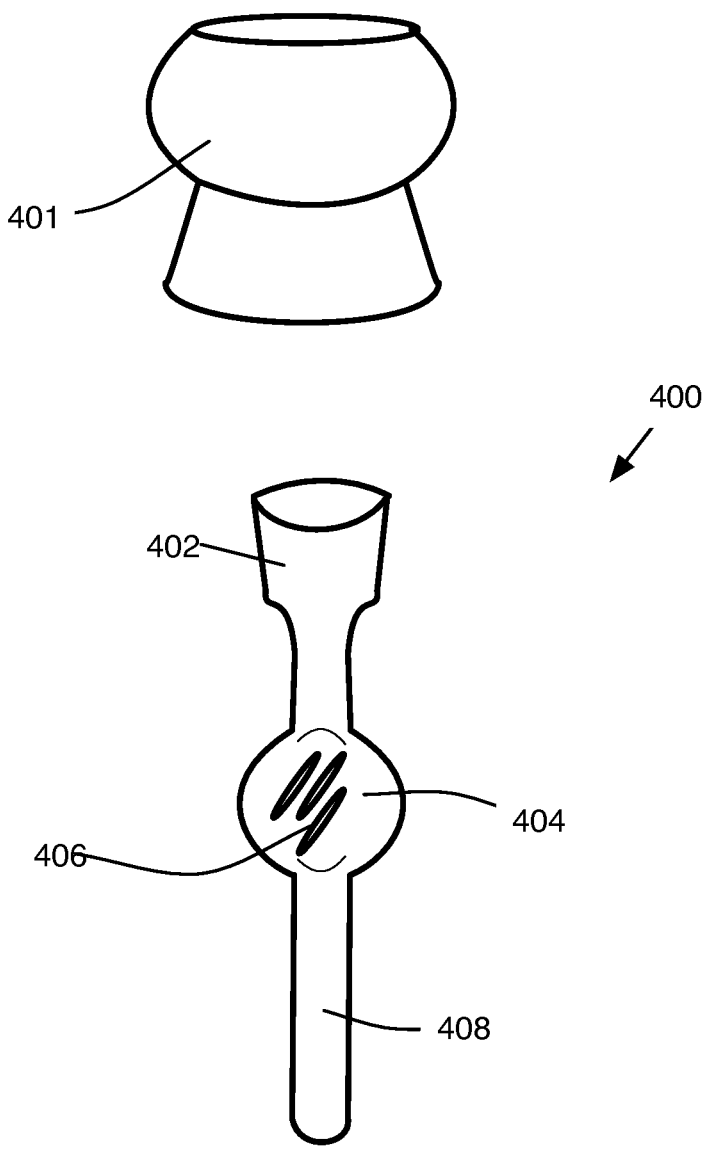
FIG. 4 is an exploded front view of a vapor cup insert according to one embodiment of the present invention.

FIG. 4 shows an alternate vapor cup insert 400 for vaporizing essential oils. It fits over a standard glassware tapered inlet, or in the inlet chamber 34 (of FIGS. 1 and 2, for example). The vapor cup includes an oil-receiving chamber 402, a sphere 404 having saw cuts 406 and a lower shaft portion 408. The vapor cup is well suited to convey vapors from volatized essential oils. The vapor cup is made from quartz tubing adapted to fit on top of a 19/26 inner joint. In use, the quartz vapor cup is preheated to a high-temperature; this temperature would damage Pyrex glass. A blown sphere beneath the vapor cup's oil receiving chamber provides adequate clearance to avoid thermal damage to the glassware in which the insert is contacting or placed. A standard chimney 401 caps the vapor cup.

In a second preferred embodiment, the chamber 26 (as described in reference to FIGS. 1-4) is adapted for use with an alternative-vaporizing platform 501 or 502; see, for example, FIGS. 5 6, and 7. The alternative vaporizing platform 501 and 502 includes a platform 503. This platform 503 is illustrated in FIG. 5, a top view along the line 5-5 of the front view in FIG. 6: However, the top view of the vaporizing platform 502 of FIG. 7 (along line 5-5 of FIG. 7) would look identical. This vaporizing platform (either 501 or 502) includes an circular, or preferably oval side wall 509 that has a larger-diameter open top defined by a top lip 507 and tapers to a narrower bottom to define a fluid conduit from the open top to a stem 513, which is a cylindrical conduit with an open top and bottom. A ring 511 is disposed between the stem and the top portion. The stem is adapted to fit on a mating conduit provided by the chamber 26 and the ring is sized to locate the platform relative to the top part of the mating conduit (not shown in FIGS. 5-7). The platform is surrounded by at least one, and preferably four, fluid conduits 505 (labeled 505a, 505b, 505c, and 505d). This enables a subject material (sample) to be dropped on a pre-heated platform, allowing instant vaporization—and the pre-heating of the platform is heated by an external heat source, such as a butane torch commonly used in the restaurant industry to make crème brulee or a standard laboratory Bunsen burner, for example. Thus, the sample transfers from solid to gas to be drawn into the stem and ultimately into the vessel 26.

Figure 8:
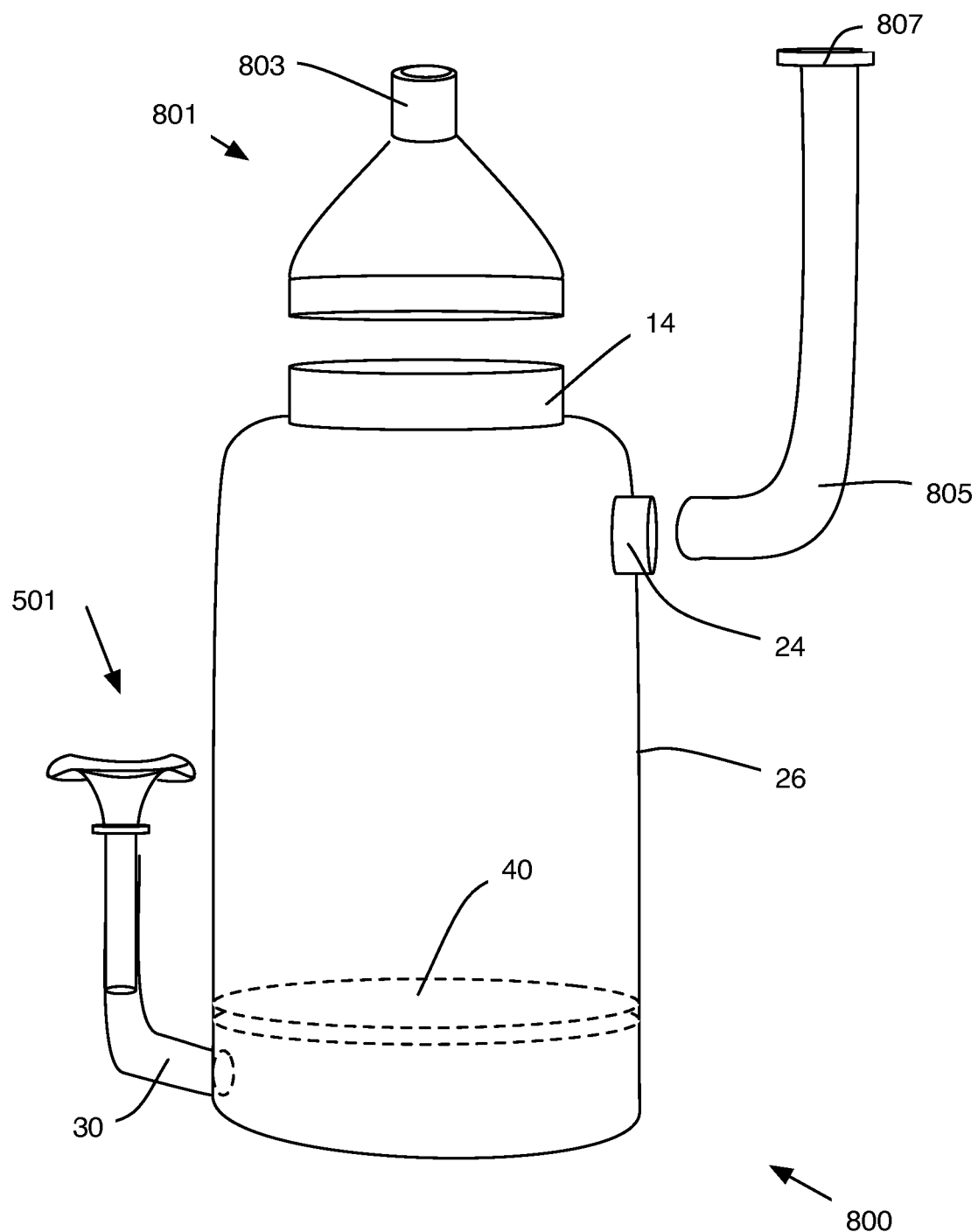
FIG. 8 is front view of a laboratory glass apparatus incorporating a vapor cup of FIG. 6.
Figure 9:
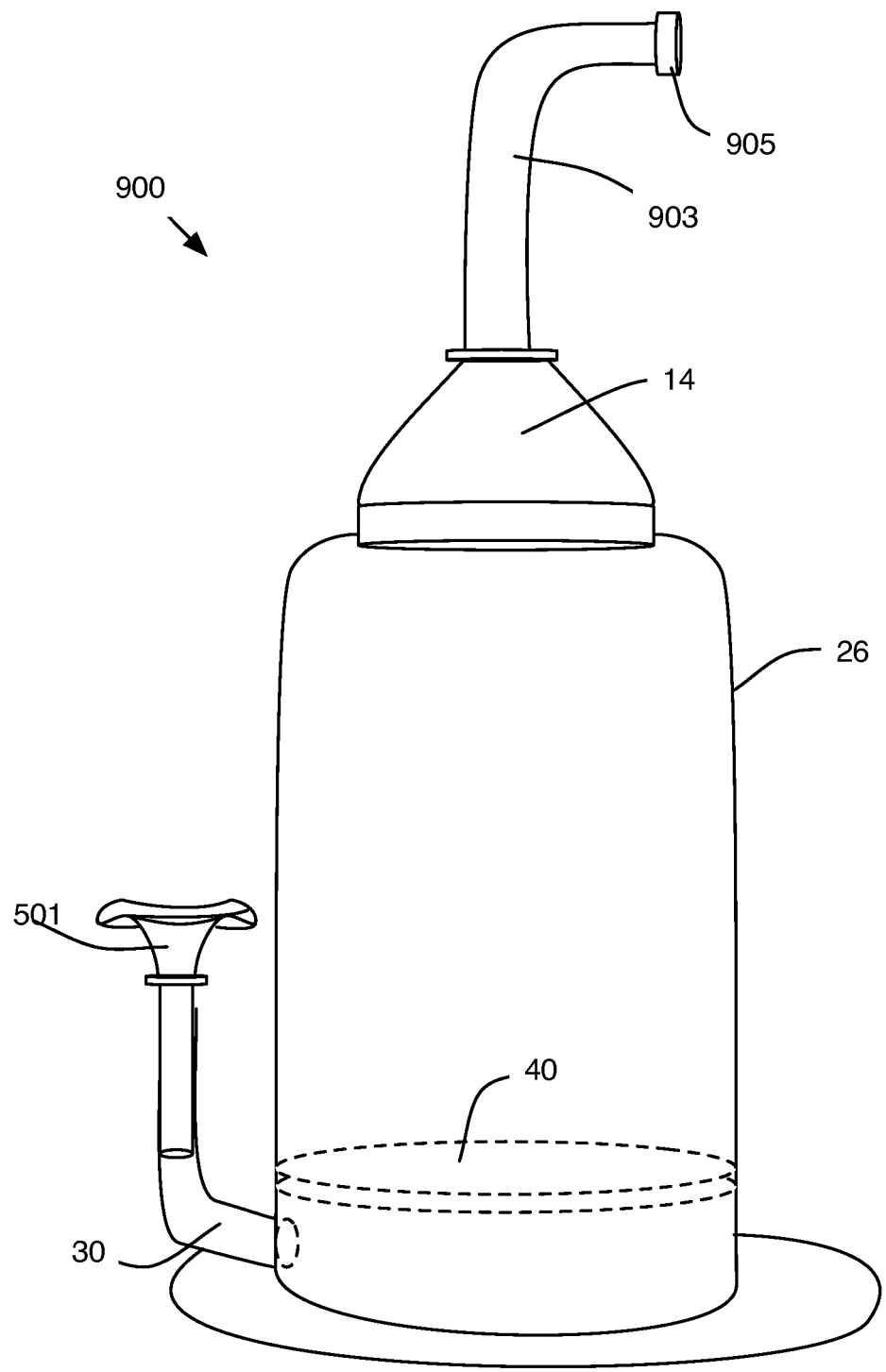
FIG. 9 is an alternative view of the laboratory glass of FIG. 8 with the components in the assembled positions.

FIGS. 8 and 9 illustrate the vaporizing platform 501 (although vaporizing platform 502 would work equally well). The vaporizing platform inserts in a downward conduit inlet 30, which positions the inlet opening below the fritted disc filter 40 inside the vessel 26. The vessel includes an open top with a splashguard 801 having a vertically extending top relief valve conduit 803. An exhaust port 24 locates below the open top and above the fritted disc. And couples to a mouthpiece 807 for drawing volatilized sample through an exit conduit 805 from the vessel 26.

With specific reference to FIG. 9, the open top receives the mouth piece 905 and exhaust conduit 903. This is a more economical-to-produce design that is otherwise similar and operates essentially the same as the vessel described in reference to FIG. 8.

Figure 10:
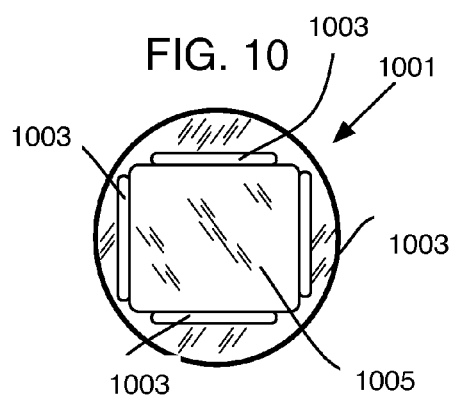
FIG. 10 is a top view of an alternative vapor cup according to another preferred embodiment of the present invention.
Figure 11:
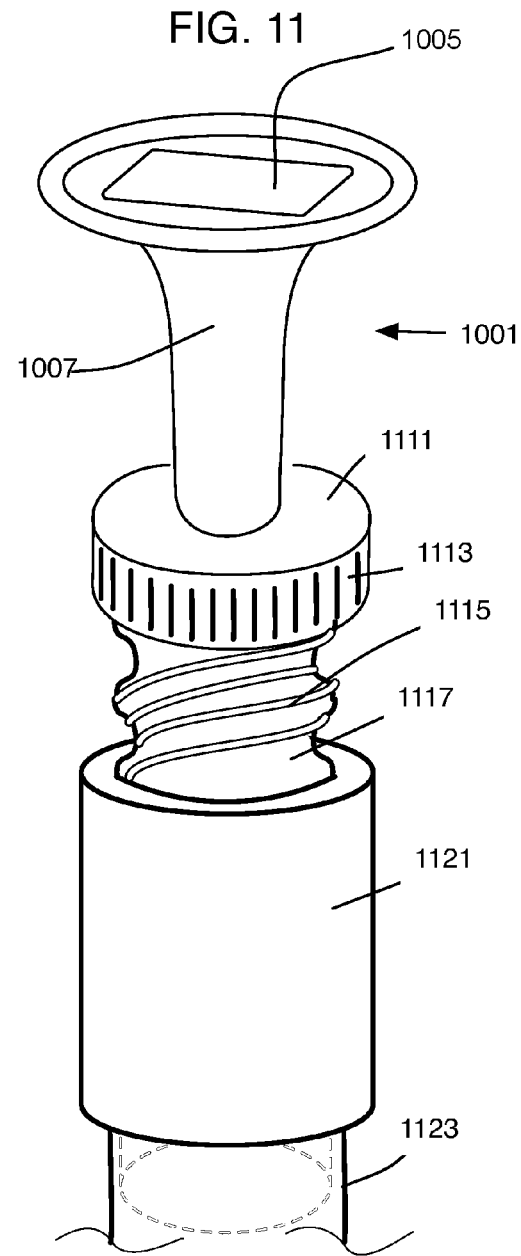
FIG. 11 is a front view of the vapor cup of FIG. 10 inserted in a laboratory glass apparatus.

FIGS. 10 and 11 illustrate another preferred vapor cup 1001 according to an alternative embodiment of the present invention. The vapor cup includes a sample tray 1005 fabricated from glass. At least one, and preferably four, slots 1003 arrange around the perimeter of the tray. A stem 1007 supports the tray at a proximal end. The tray, or vapor cup, is adjustable for height, passing through a threaded plastic or nylon compression fitting (such as an Ace Thread or similar) and secured at an intended height by means of an O-ring, which is compressed against the quartz tube by the threaded inset compressing it as it descends the glass thread. Using a standard "Ace" thread allows the quartz vapor cup to sit at a predetermined burner-height to keep the burner flame sufficiently far away that the borosilicate apparatus is not exposed to a temperature in excess of its service limit.

In a preferred embodiment, a compression thread arrangement, for example an "Ace" thread (available at www.ace-glass.com/featured/ace_threds/ace_threds.pdf) is used. This type of thread is well understood in the industry and includes a nylon or PTFE insert that engages glass threads of a predetermined and pre-mated size. At a distal end, a compression ring (O-ring) locates to seal a small gap between the insertion tube carried by the nylon or PTFE insert. Other arrangements would work equally well. As shown in the drawing, the distal end of the stem passes through a threaded portion 1117, which includes a male thread 1115, which adapts to mate to a corresponding female thread (not shown in the figures) located inside the coupling device 1121, which is attached in turn to the downward directed conduit 1123. (This is the same or similar conduit to the conduit 22 of FIGS. 1, 2, and 3, for example). An adjusting means 1113 couples to the vapor cup so that clockwise turning lowers the sample tray toward the conduit 1123 and anti-clockwise rotation lifts the tray away from the conduit. In this way the tray can be optimally positioned relative to a heat source (not shown), such as a Bunsen burner or gas or butane torch. The slots 1003 allow the vapor from the heated sample in the tray to be drawn in to the conduit when a negative pressure is drawn, for example. This arrangement of vapor cup contemplates only the use of one fritted disc the main body of the vessel.

Figure 12:
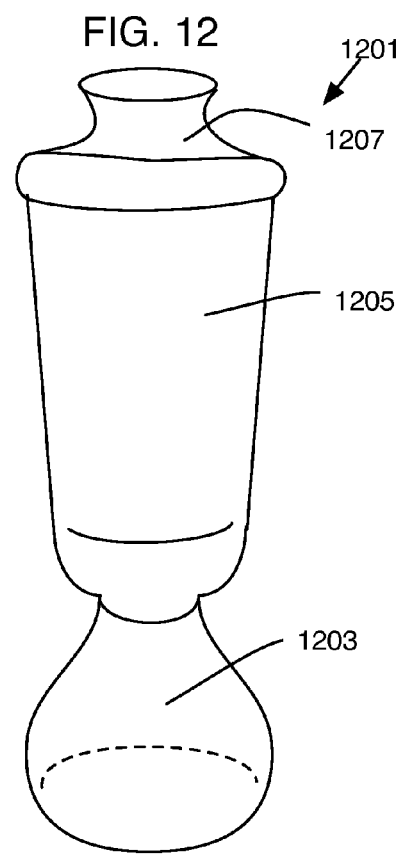
FIG. 12 is a front view of a lid for a laboratory glass apparatus.

FIG. 12 is a lid 1201 for laboratory glass apparatus such as illustrated in FIG. 1, 2, or 3. The lid includes a splashguard 1203 at a distal end, an intermediate taper portion 1205 having an industry standard taper as would be appreciated by those skilled in this art, and a handle portion 1207 at a proximal end. The laboratory glass vessel would be adapted to have an open top with a matching taper, as would be understood in the art. One advantage of the open top is that it facilitates cleaning of the interior chamber of the vessel.

To provide more optimal scrubbing of particulates from the vapor, it is often desirable to elevate water temperature above tap water ambient, and maintain elevated temperature throughout the process to selectively condense undesired particulates or gaseous factions. Warm water prevents or controls condensation of VOC's in the vapor sample. Accordingly, it is contemplated that the various embodiments of the present invention may be placed in a water jacket with circulating water that maintains this temperature. Other means of heating the water and vessel include heating the apparatus in an oven and then placing an insulated jacket around it, for example. Or otherwise enhancing the homo-thermic characteristics of the vessel, as would be understood in this art include a vacuum jacket.

Although the invention has been particularly shown and described with reference to certain embodiments, it will be understood by those skilled in the art that various changes in form and detail may be made without departing from the spirit and scope of the invention.

I claim:

1. A glass vessel apparatus comprising:
    an inlet chamber having an open top and having a downward extending conduit;
    an exhaust chamber defined by at least one sidewall coupled to a bottom wall and the at least one sidewall defining an open top, wherein the exhaust chamber is adapted to hold a liquid,
    the exhaust chamber further includes a fritted disc filter and an aperture, the aperture located adjacent to the bottom wall and coupling to the downward extending conduit of the inlet chamber, the aperture being arranged on the at least one sidewall below the fritted disc filter; and
    a fritted disc pre-filter adapted to couple the inlet chamber to the downward extending conduit.

2. The apparatus of claim 1, wherein the apparatus further comprises:
    a vapor cup having a top lip, the vapor cup adapted to insert in the open top of the inlet chamber, wherein the vapor cup comprises:
        a ring adapted to rest on the open top of the inlet chamber,
        a stem extending downward from the ring and adapted to be inserted inside the downward extending conduit of the inlet chamber, and
        a platform arranged in the center of an open top of the vapor cup, the platform having at least one fluid conduit disposed between one side of the platform and an inner wall of the vapor cup.

3. The apparatus of claim 2, wherein the vapor cup comprises:
    a tray supported on a proximal end of a stem, the tray having at least one slot adapted to provide a fluid conduit from an exterior portion of the stem to an interior conduit inside the stem;
    a threaded portion arranged on a distal end of the stem; and
    an adjusting mechanism coupled to the thread; and
    wherein the glass vessel is adapted to selectively receive the threaded portion whereby rotation on the adjusting mechanism causes the relative position of the tray to move from a first position to a second position.

4. The apparatus of claim 1, wherein the glass vessel comprises borosilicate glass.

5. The apparatus of claim 1, wherein the exhaust chamber further comprises a relief valve disposed on the at least one sidewall and a mouthpiece, the mouthpiece being adapted to attach to the relief valve disposed on the at least one sidewall.

6. The apparatus of claim 1 further comprising:
    a cleaning portal with a splash guard adapted to selectively couple to the open top.

7. The apparatus of claim 6, wherein the splash guard further includes a relief valve conduit arranged on a top portion of the splash guard and extending upward therefrom and a mouthpiece, the mouthpiece being adapted to attach to the relief valve conduit of the splash guard.

* * * * *